United States Patent [19]
Janus

[11] Patent Number: 6,068,616
[45] Date of Patent: May 30, 2000

[54] DRUG INJECTION SYSTEM WITH SELF-ASPIRATION FEATURE

[76] Inventor: Stan Janus, 133 Madoc Drive, Brampton, Ontario, Canada, L6V 2A5

[21] Appl. No.: 09/120,282

[22] Filed: Jul. 22, 1998

Related U.S. Application Data

[63] Continuation-in-part of application No. 08/640,465, May 1, 1996.
[51] Int. Cl.[7] .................................................. A61M 5/00
[52] U.S. Cl. ........................ 604/240; 604/187; 604/201; 604/227
[58] Field of Search .................................... 604/181, 187, 604/200, 201, 218, 227, 232, 234, 239–243

[56] References Cited

U.S. PATENT DOCUMENTS

2,691,372  10/1954  Lores ....................................... 604/234

*Primary Examiner*—Wynn Wood Coggins
*Assistant Examiner*—Deborah Blyveis

[57] ABSTRACT

The present invention provides in part an improved drug injection system, comprising novel self-aspirating syringes, drug cartridge and novel needle assemblies. It is primarily intended for administering of local anesthetic by dentists, but it can be used equally well in medical and veterinary applications. In one aspect, the novel syringe is made lightweight, comfortable to hold and corrosion resistant. In another aspect, some novel changes in the design of the syringe reduce the possibility of transmitting an infection from the blood of one patient into the blood of another. Additionally, innovation in the design of needle assembly makes the syringe safe to use even without prior sterilization and at the same time eliminating the possibility of transmitting infection as the result of human error.

11 Claims, 5 Drawing Sheets

DRUG INJECTION SYSTEM WITH SELF-ASPIRATION FEATURE

This application is a continuation-in-part of application Ser. No. 08/640,465 filed May 1, 1996.

FIELD OF INVENTION

Drug injection system, including instruments such as self-aspirating syringes and needles for them, for dental, medical and veterinary applications.

BACKGROUND OF THE INVENTION

In the dental, medical and veterinary field, the now commonly used syringes are of two kinds: disposable and non-disposable. Disposable syringes are economically practical, that is they are cheap and of simple design, typically consisting of just two parts made from plastic. However, many drugs to be injected come in pre-sterilized single use cartridges which, in general, cannot be used in disposable syringes. As the syringe has to be more complicated to adapt it for use with the cartridge, it is more expensive to manufacture and hence it is non-disposable. Many re-usable syringes which incorporate facility for the manual or for automatic aspiration are even more complicated and they commonly are made from metal, which is usually chrome plated brass.

Self-aspirating syringe for use with drug cartridge is described in the U.S. Pat. No. 3,583,399. Since its invention, self-aspirating syringe have became popular among dentists and are now used world wide. The syringe described in the patent has a thumb rest on the end of a plunger rod. The now popular design of this syringe has a thumb ring on the end of plunger rod, rather than a thumb rest. The syringes of the prior art are made by machining them from metal tubing or from solid metal bars.

Such prior art self-aspirating syringes, however, still have drawbacks. A dentist, while holding the syringe in fingers of his (or her) hand, has to insert the needle in a precisely selected spot in the patient's gum for injection of local anesthetic. Selection of the spot with precision is important, because the needle must not hit a blood vessel. To use the syringe the dentist places the thumb in the thumb ring which in self-aspirating syringes of the prior art looks like a piece cut off from a metal tube. Having a cylindrical inside surface and thin edges makes it uncomfortable to hold.

It is quite common that the dentist works with an assistant. After completion of injection of local anesthetic the dentist swings his (or her) arm sideways to hand over the syringe to the assistant. The dentist's thumb at this time is still trapped in the thumb ring. While the assistant grabs the syringe by its barrel and pulls it off, the thin edge of the thumb ring may press strongly into the thumb, hurting it or else causing a discomfort.

In use, the needle, mounted on the end of syringe barrel, punctures the diaphragm in the drug cartridge. It has been observed that in the self-aspirating syringe it is much more likely that the drug may leak through the puncture. Leakage may not occur every time, it could be very small and not readily visible, yet, nonetheless, it can have important consequences. Even a tiny leak can be a potential carrier of infection from the blood of one patient into the blood of another. While the standard procedure of sterilization of syringes between patients prevents the potential, it still can come into effect by accident.

Dentists usually have more than one syringe and all of them could be identical. On the average, a dentist administers injections to about one thousand patients a year. A human error is possible and a used syringe may be mistaken for a sterilized one.

Another problem with non-disposable syringes of the prior art is corrosion. Exposure to the drug, which is corrosive to metals, to steam and to sterilization temperatures eventually corrodes syringes made from chrome plated brass and the plating flakes off. While the syringe parts made from stainless steel alleviate this problem, stainless steel is more expensive to use.

SUMMARY OF THE INVENTION

One object of the present invention is to break with the tradition of making non-disposable syringes mainly from metal and to adapt advanced manufacturing technology to make syringe parts from non-metallic materials.

Another object of the invention is to enable the dentist to exercise better control of the syringe by making it more comfortable to hold and by making it lighter.

Another object of the invention is to reduce drug leakage through the puncture in the diaphragm of the cartridge by making several modifications in the syringe design.

A further purpose of the invention is to prevent the possible transmitting of infection from one patient to another without the need to sterilize the syringe for every new patient, yet still retaining the feature of self-aspiration.

As described in detail in the disclosure, attaining the stated objects results in a more complicated mechanical design of the product. In spite of that, due to the application of the new manufacturing technology, inherent in this invention, all objects are attained without increasing manufacturing costs. This includes light weight of the instrument and its resistance to corrosion.

The present invention also provides means to eliminate the need to sterilize the instrument. This is achieved by singling out parts of the drug injection system which can possibly transmit the infection and by combining them with the needle assembly which is commonly used once anyhow. The means are novel design of the needle assembly and the matching modifications of the syringe itself.

The resulting benefits to dentists are several. There are no more items to dispose than in the prior practice. Installation and removal of needle does not take any longer. There are substantial savings in elimination of sterilization. There is no chance of an error. Moreover, there is relief from the mental stress of constantly making sure a non-sterilized syringe is not mistaken for a sterilized one.

BRIEF DESCRIPTION OF DRAWINGS

Preferred embodiments of the present invention are illustrated in the attached drawings in which:

FIG. 13 Is the same cross section as in FIG. 10, but with cartridge inserted and shown in larger scale.

FIG. 15 Is a plan view of the thumb ring of the prior art.

DEFINITION OF TERMS AND PRELIMINARY INFORMATION

In order to appreciate the differences between the self-aspirating syringes of the present invention and the ones of the prior art, it will be described first how the drug injection system works, that is what is common to both. The major components of the injection system are the syringe, the drug cartridge and the needle assembly, which we shall call also a "needle". They are all equally essential to the proper operation. The interaction between them is what produces the desired result.

Self-aspirating syringes of the prior art and of the present invention are similar in appearance and have corresponding parts which perform the same or similar function. Corresponding parts in both will have the same name and the same part number, the difference being that part numbers in the syringe of the prior art have the prefix 1-, whereas the prefix 2- will be used with part numbers of the syringe of the present invention. Part numbers with no prefix refer both to the syringe of the prior art and the present invention.

Figure 1:
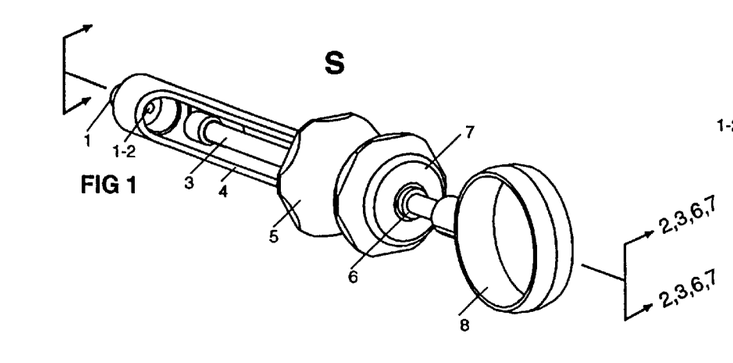
FIG. 1 Is a perspective view of one embodiment of self-aspirating syringe of the present invention.
Figure 2:
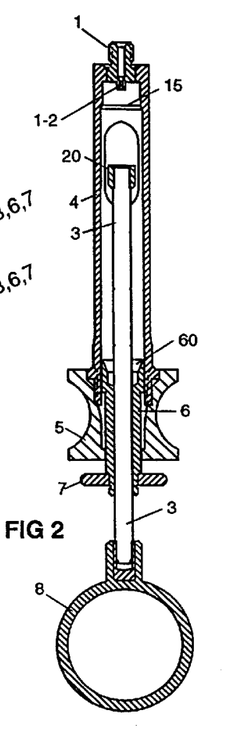
FIG. 2 Is a longitudinal section of the syringe of FIG. 1.
Figure 3:
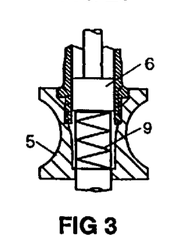
FIG. 3 Is a longitudinal section of the finger grip of FIG. 1 showing spring.

Syringe S shown in FIG. 1 is the first embodiment of the present invention. The term "syringe" without S, can refer to either the prior art or the present invention. With reference to FIG. 1, FIG. 2 and FIG. 3, parts of the syringe, which will be referred to in the description, for both the prior art and the syringes of the present invention are:

1. Needle holder
2. Bumper post or bumper
3. Plunger rod

4. Barrel
5. Finger grip
6. Guide bushing
7. Push disk
8. Thumb ring
9. Compression spring The barrel 4, finger grip 5 and thumb ring 8 are different in syringes of the prior art and of the present invention. Some of the needle holders 1 in syringes of the present invention are different from those of the prior art. The procedure of the drug injection will be described first, to be able to explain better what are its shortcomings. This procedure, as such, is the same for the self-aspirating syringes of the prior art and of the present invention.

Figure 4:
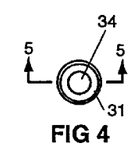
FIG. 4 Is an end view of typical drug cartridge.
Figure 24:
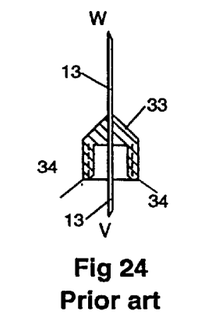
FIG. 24 Is a longitudinal section of the needle assembly of FIG. 23.

The self-aspirating syringe, similar to one in FIG. 1 is used in conjunction with a needle assembly 24, FIG. 24, and drug cartridge 31, FIG. 4. The latter is inserted into the barrel 1-4, FIG. 6. The procedure of making an injection and the events to be described are the same if the barrel is 2-4, FIG. 7, that is the one of the present invention. The cartridge 31, FIG. 4, has a round, transparent tubular shell 32, FIG. 5. This shell is closed off on one end with a rubber diaphragm 10, which is held in place by an aluminum cap 11, crimped around the flange of the shell. The cap has an opening in the center, to expose the diaphragm 10. The other end of the shell is closed off with a rubber piston 12 which can be pushed deeper into the body with plunger rod 3, FIG. 1.

Figure 6:
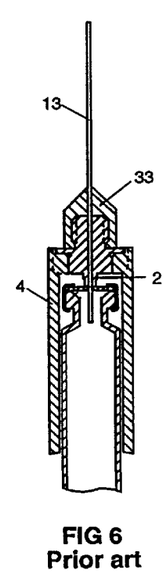
FIG. 6 Is a longitudinal section of syringe barrel of the prior art, showing the diaphragm prior to injection.

After the needle assembly 24 has been attached to the needle holder 1, FIG. 1 and FIG. 6, the cartridge is inserted into the barrel 4. The cartridge is then pushed towards the needle, so that the latter pierces the diaphragm. The needle holder has an extension on the inside of syringe, a post 2, which acts as a bumper. The needle passes through a hole in the center of the post. After the needle has pierced the diaphragm, the diaphragm eventually ends up touching this post. The resulting configuration is shown in FIG. 6. After this initial set up, the syringe is ready to be used by the dentist for injection of local anesthetic.

The dentist must make sure that the needle does not hit a blood vessel, because then the local anesthetic is carried to other parts of the body (including the brain), which presents a hazard to the patient. The dentist can avoid it by first making an aspiration test.

To make the test, the dentist presses disk 7, after having inserted the needle into the patient's gum. The guide bushing 6 transmits the thrust from the disk 7 directly to the shell 32 of cartridge, pushing it towards the needle holder 1. When the diaphragm 10 is pushed against the bumper 2, FIG. 7, it deflects and forces a small volume of drug out of the needle and into the patient's gum.

When the pressure on the disk 7 is released, the rubber diaphragm 10 springs back, aspirating automatically exactly the same volume of liquid as was injected. If the needle has hit a blood vessel, blood can be seen in the transparent cartridge. The piston 12 in the cartridge was not pushed and it did not move, so that the net injected volume is zero. This is called aspiration before injection. If blood is visible in the cartridge, dentist has to re-insert the needle at another spot on the gum.

To proceed with injection, the dentist presses on the thumb ring 8 which is on the end of plunger rod 3, FIG. 1. The rod moves the rubber piston 12 in the cartridge, FIG. 5. This way any desired volume of drug can be injected. The dentist does it in several steps, with pauses in between steps. While the piston is pushed in, because of the internal friction, the whole cartridge is pushed against the bumper 2 and the diaphragm 10 is deflected inwards thereby, FIG. 7. During a pause, when the pressure on the thumb ring is relieved, the diaphragm springs back. Aspiration takes place automatically as many times as there are pauses in the injection process.

The drug is forced out through the needle, because the pressure is created inside of-the cartridge. The same pressure can also cause the drug to leak out through the puncture in the diaphragm 10 and be deposited on the bumper 2, FIG. 7. During aspiration, the pressure in the cartridge is negative and this may cause sucking back in through the puncture what was deposited on the bumper before. Several cycles of alternation between positive and negative pressures inside the cartridge can take place during one injection procedure. Every time a liquid deposited on the bumper from preceding leak can be sucked back into the cartridge through the puncture in the diaphragm.

What is sucked back into the cartridge from the bumper 2 may be injected back into the patient during the next high pressure portion of the cycle in the same injection procedure. The point is that, if the syringe has not been properly sterilized between patients, some of the deposit on the bumper 2 could have originated during a preceding injection procedure on another patient. This is a path along which an infection present in the blood of one patient can be passed into the blood of another. Herein lies a danger for the patient, if the syringe has not been sterilized between different patients. Unknowingly, the patient can be infected with a dangerous disease such as AIDS.

After this introduction it is possible now to describe what is novel in the syringe of the present invention.

DETAILED DESCRIPTION OF FIVE EMBODIMENTS OF THE INVENTION

The present invention consists of four novel developments:

1. Reduction of drug leakage through the puncture in diaphragm of cartridge to reduce the risk of cross-infection.

2. Making syringe more comfortable to hold.

3. Adaptation of new manufacturing technology to this product, to make the attainment of developments 1 and 2 economically feasible and also to make the syringe lighter and corrosion resistant.

4. Elimination of the need to sterilize the syringe for each new patient.

Different means to achieve this are presented in five embodiments of the invention. The preferred embodiment is described as the fifth one, because it is the easiest logical way to do describe the embodiments in this sequence.

Novel ideas which make this possible will be singled out and stated separately in the disclosure.

THE FIRST EMBODIMENT

FIGS. 1 and 2 show the assembly of all parts of syringe of the first embodiment of this invention. The needle holder 1, fastened to the end of barrel 4, is a round (that is rotational) body. As such, it has an axis of symmetry which is its centerline. The needle holder 1 has a hole on its centerline for the passage of needle. The needle itself is a part of a disposable needle assembly, shown in FIG. 24. This ensures that when the needle assembly is screwed onto the needle holder, FIG. 7, the intake end of the needle V, FIG. 28, protruding into interior of the barrel, is on the centerline of barrel.

The same holds true when the needle assembly is screwed onto the barrel of syringe of the prior art, FIG. 6. Although the needle is on the centerline of barrel in the syringe of the prior art, the drug cartridge may not be. Reasons for it will be explained below. As a result, the needle may puncture the diaphragm of the cartridge off its center. This is the main reason for the leakage of drug through the puncture and all the undesirable consequences it may entail. One of the objects of this invention is to reduce the possibility of drug leakage through the puncture.

REDUCTION OF DRUG LEAKAGE

The centerline of the barrel is defined as being coincident with centerline of the needle holder (which is also the centerline of the needle) and the centerline of the external thread on the end of barrel which attaches to the finger grip. This external thread will be referred to later as "finger grip attachment means".

The fact is that due to the manner how the syringe barrels are manufactured in the prior art, the inside dimensions of the syringe barrel are larger than the size of the cartridge and hence the cartridge is loose inside the barrel.

Figure 8:
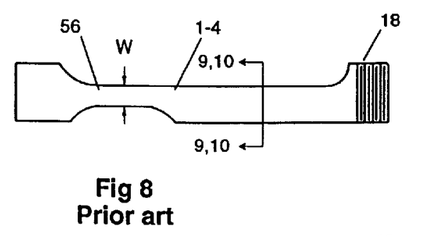
FIG. 8 Is a side view of the barrel of a syringe of the prior art.
Figure 9:
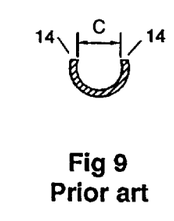
FIG. 9 Is a cross section of the barrel of syringe of FIG. 8.

FIGS. 8 & 9 show the barrel 1-4, that is one of the prior art. It is made usually from round metal tubing. The two edges 14 of the large opening in the barrel, FIG. 9, are spaced apart just enough to be able to insert cartridge into the barrel. The width of opening C, FIG. 9, is just a little more than the outer diameter of the cartridge shell 32, FIG. 5. With the barrel made from round tubing, it is necessary that the plane passing through the two edges 14 is spaced by distance F away from the center of barrel, FIG. 10. Otherwise, the width W of the link 56 between two openings in the barrel, FIG. 8, would be too narrow to resist breakage.

Spacing C, being the length of a chord in a circle (inside walls of the barrel), obviously must be smaller than the inside diameter of the barrel. Therefore, when the cartridge is inserted into the barrel, there is a large clearance 16 between the cartridge and the inside wall of the barrel, FIG. 8. This is the inevitable consequence of the barrel being made from round tubing.

Figure 10:
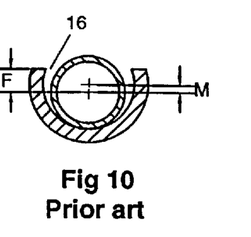
FIG. 10 Is the same cross-section as in FIG. 7, but with cartridge inserted and shown in larger scale.

A further consequence is that with the cartridge laying in the barrel as shown in FIG. 8, it is misaligned with respect to centerline of the barrel by distance M, FIG. 10. The dentist has no means of centering it. Thus, when the cartridge is pushed up against the needle, it may puncture the diaphragm off center.

It has been observed that elastic forces in the rubber diaphragm tend to contract the puncture. Needle 13 passes through the center of bumper 2, FIGS. 6 and 7. If the bumper presses the diaphragm in the center, these elastic contracting forces in rubber are sufficient to seal around the needle, so that no leakage of drug occurs. It has been observed that the leakage frequently occurs if the bumper presses on the diaphragm off center.

The more the bumper is touching the diaphragm off center, the greater is the leakage. The explanation of it is thought to be that the deflection of the rubber diaphragm 10 by bumper 2 creates stretching forces in it. If the bumper is pressing on the diaphragm off center, these stretching forces on the diaphragm are greater on one side of the needle than on the other. On the side where the stretching forces are greater, they overcome contracting forces in rubber, the puncture becomes elongated and the leakage around the needle occurs. The remedy is to provide for better alignment of the cartridge with the centerline of the barrel.

Figure 11:
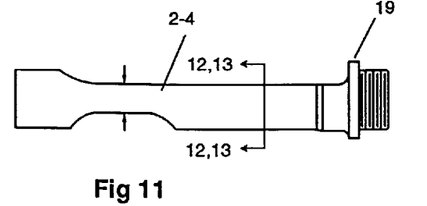
FIG. 11 Shows the barrel of the syringe of FIG. 1.
Figure 12:
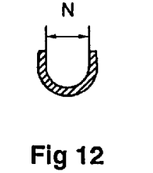
FIG. 12 Is a cross section of barrel of FIG. 11.

In the first embodiment of the present invention the barrel 2-2, FIGS. 11 & 12, has a U shaped cavity for the accommodation of cartridge. The obtain the U shape, the barrel is not made from metal tubing but rather it is molded from a non-metallic material which is resistant to corrosive effects of chemicals and sterilization temperatures. The distance N, FIG. 12, between the legs of U is just large enough to insert the cartridge. The center 28 of rounding in the bottom of U, FIG. 13, coincides with the center of the cartridge shell 32, FIG. 5, and both are made to coincide with the centerline of the barrel. To center the cartridge all the dentist has to do is to press the cartridge into the bottom of U.

In the first embodiment the cross section of the cavity inside of the barrel for accommodation of cartridge has the shape of the letter U, the legs of the U being approximately parallel, the spacing between the legs of the U being slightly more than the outside diameter of the standard cartridge, the bottom of the U being such that the cartridge laying on it is centered with respect to the centerline of the barrel.

Although the U shape of cavity in barrel alleviates the alignment problem, it does not solve it completely. The cartridge is still free to move between the legs of U. This problem is solved with two other novel ideas, one for the diaphragm end, the other for the piston end of the cartridge. According to DIN standard for cartridges, the aluminum cap 11, FIG. 5, has a smaller OD (outside diameter) than the OD of cartridge shell. With the aluminum cap being made by stamping, the dimensional variation of the OD of the cap is much smaller than of the OD of cartridge shell. This makes the cap well suitable for centering the cartridge on it.

In the barrel 2-4 of the present invention, the cross section of the cavity changes from shape U to a closed circular one next to the bumper where the cap 11 is located during the injection procedure. See FIG. 7. At this spot cavity in the barrel is smaller, such that it is a close fit for the cap all around. It is visible as a step 15 on inner wall of the barrel, FIGS. 2 & 7. As is visible in FIG. 6, on the same spot in the syringe of the prior art there is no such step down in the size of the cavity, since the inside diameter of the tubing remains the same over the entire length of the barrel.

In the first embodiment the cavity in the barrel in proximity of the bumper is cylindrical of smaller inside diameter than the rest of the barrel, such as to provide a close fit for the cartridge cap.

Figure 14:
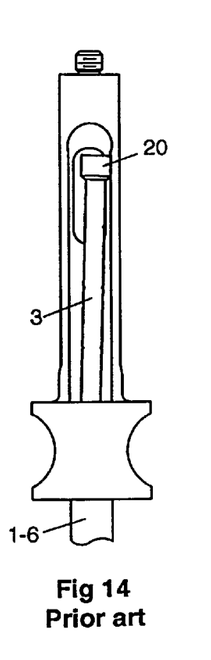
FIG. 14 Shows schematically the misalignment of the plunger rod in the syringe of prior art.

It has been observed during the manufacture of syringes of the prior art, that the plunger rod 3, when fully pushed in, in some syringes was angularly misaligned with the longitudinal axis of the syringe, as shown on FIG. 14. This was occurring at random and the cause was traced to the threaded connection between the barrel and finger grip.

In general, there must be an ample clearance between the internal and external threads in mating parts to be able to screw in one part into another. In the barrel 1-2 of the prior art, FIG. 6, the external thread 18 on its end has approximately the same OD as the rest of the barrel.

Figure 22:
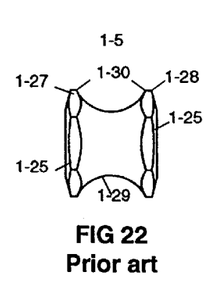
FIG. 22 Is a side view of the finger grip of the syringe of the prior art.

When the barrel 1-2 of the prior art is screwed in tightly into the fingergrip 1-5 of the prior art, FIG. 22, the end of thread (which is a point on the circumference) serves as a stop. Since there is clearance between internal and external threads, this may tilt the barrel to one side, FIG. 14.

To provide control of alignment between the barrel 2-4 and the fingergrip 2-5 of the present invention, a flange 19 is added to the barrel 2-4, FIG. 11. It fits into a recess 17 in the fingergrip 2-5, FIG. 18. When the barrel is screwed in, the flange rests against the bottom of recess 17, or a flat end face of the finger grip (if there is no recess). The end of barrel with the flange and external thread on its end has an axis of symmetry, which is its centerline. The flat mating surfaces on both the flange and the finger grip are at right angle to the centerlines of their corresponding parts. The center line of the finger grip is the centerline of the round hole in it. The joint, as described, ensures that the centerlines of the barrel as a whole and of the finger grip coincide.

When the flange 19, FIG. 11, is tightened upon assembly against its seat on the finger grip, this assures proper alignment of the barrel with the finger grip. Consequently, this assures that the centerlines of the guide bushing 2-6, FIG. 2, and of the plunger rod 2-3 coincide with the centerline of the barrel 2-4. The plunger rod has a head 2-20 which during injection enters the inside of the cartridge on its end to push the piston. This and the inside taper 2-60 on the bushing, FIG. 2, help to keep the piston end of the cartridge on the centerline of the barrel. Functional part of the flange is its seating surface and it can be provided also as a step down or a shoulder on the OD of barrel.

In the present invention the provision of a flange next to the external thread on the end of barrel and the provision of the corresponding mating surface on the finger grip contributes to keeping the centerline of the cartridge in alignment with the centerline of barrel.

The reduced inside diameter 15 of the barrel close to the bumper 2, FIG. 2, U shaped cavity in the midrange of the barrel, FIG. 13, and the flange 19 on the end of barrel, FIG. 11, in combination keep the whole of the cartridge on the centerline of the barrel. This ensures the best possible centering of the diaphragm 10 with the bumper 2. As a result, this reduces the possibility of leakage of drug through the puncture in diaphragm and the consequent risk of cross infection to the patient.

MAKING SYRINGE MORE COMFORTABLE TO HOLD

Figure 16:
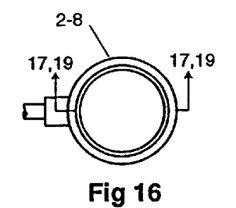
FIG. 16 Is a plan view of the thumb ring of the present invention.

The thumb ring of the prior art is shown on FIG. 13. As was mentioned in "Background of the invention", thin edges of the ring of the prior art make it uncomfortable to hold. With the thumb inside of the ring of the prior art, when pushing it in the direction A, FIG. 16, as happens when making an injection, the contact between the thumb and the ring is limited to a small area 21 on the thin edge of ring. Concentration of pressure on small area of skin makes it uncomfortable.

Figure 18:
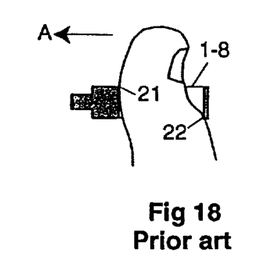
FIG. 18 Is a cross section of thumb ring of FIG. 15 with thumb in it.

Something similar happens in the situation when the syringe is pulled off the dentist's hand by an assistant also in direction A, FIG. 18. In this case the pressure on the skin is in a small area of contact 22. Because in this situation the thumb is trapped in the ring and the pulling off may occur quickly, the thumb may get hurt.

Figure 17:
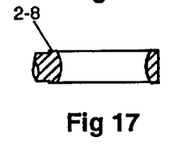
FIG. 17 Is a cross section of thumb ring of FIG. 16.
Figure 19:
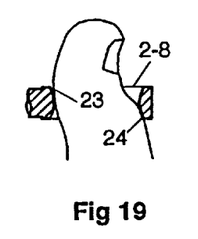
FIG. 19 Is a cross section of thumb ring of FIG. 16 with thumb in it.

In the present invention the thumb ring 2-8 has a toroidal-like surface on the inside of its opening, FIG. 17 and 19. It is not unlike the surface in the hole in a ring doughnut. The ring 2-8 does not have thin edges. In the same situations as described in the foregoing, the pressure of ring on the skin is distributed over larger contact areas 23 and 24, FIG. 19. Tests have confirmed that the thumb of the present invention feels much more comfortable to hold than the ring of prior art.

Figure 20:
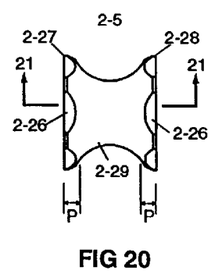
FIG. 20 Is a side view of the finger grip of the syringe of FIG. 1.
Figure 21:
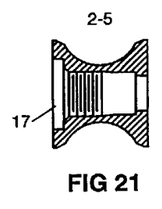
FIG. 21 Is a longitudinal section of the finger grip of FIG. 20.

The present invention includes also refinements in the shape of the finger grip. The common shape of the finger grip of the prior art is shown in FIG. 19 and the shape of the one of the present invention is shown in FIG. 20. They both have the same overall length along the longitudinal axis. The finger grip of the prior art has conical surfaces 1-25 on both ends to give it a more rounded appearance. The finger grip of the present invention has flat surfaces 2-26 on each end. The idea is to space further apart the outer edges 1-27 and 1-28, without increasing the length of finger grip and also to eliminate edges 1-30. Spacing the outer edges 1-27 and 1-28 further apart (which correspond to edges 2-27 and 2-28 in the finger grip of the present invention) gives more room for the index and middle fingers to grip this part.

In both finger grips 1-5 and 2-5 of the prior art and the present invention respectively, the surface between the edges 1-27 and 1-28 is an annular concave shape (inverse toroidal). In the finger grip of the present invention the increased spacing between these two edges is used to make a transition from the concave surface 1-29 to an annular convex one in the areas P close to edges 2-27 and 2-28, FIG. 20. The idea is to keep the fingers away from edges and to enlarge the contact area between the fingers and the finger grip by making a gradual transition from the concave surface to the convex one. This eliminates contact spots on edges of the finger grip of the prior art where there was concentrated pressure on the skin. Tests have confirmed that the finger grip of the present invention is more comfortable to hold.

The assembly of finger grip and barrel can be molded as one piece. Whether it will be done so or not, is mainly a matter of economic considerations.

CORROSION RESISTANCE, LIGHT WEIGHT, VALUE

To make the syringe barrel of the present invention from metal by machining in the shape as described (with a step on inside diameter, of U cross section and with a flange) would be far more costly than making the barrel of the prior art shown in FIG. 8. The same applies to making the thumb ring with a boss and with a toroidal inside surface. Also, it could not be alternatively produced by die casting, because metals which can be die cast do not have good enough corrosion resistance. There would be no market for the syringe as described made from metal because of its prohibitive cost.

The present invention provides for the manufacture of syringe parts by molding. It is a superior idea in the sense that it makes the practical implementation of the novel features of the present invention economically feasible. Major parts of the syringe of the present invention are injection molded from engineering plastic with good mechanical strength, with good resistance to corrosive effects of the drug and various aggressive germicides. The moldable material must withstand also sterilization temperatures (up to 180 deg. or higher). Such material may be preferably PPS (polyphenylene sulfide). Other suitable moldable materials are PEEK (polyether ether ketone), PET (polyethylene terephtalate) and LCP (liquid crystal polymer). These materials may be compounded with commonly used reinforcing additives. The syringe is much lighter than one made from metal which makes it more comfortable to use.

The present invention is the first application of engineering plastic, such as PPS, in making syringe barrels by injection molding. It is much better than chrome plated brass, because plating starts to peel off from repeated sterilization.

There are four other embodiments described. They all have in common a major feature which is not present in the first embodiment. The difference between them is how this feature is implemented. The fourth embodiment is the preferred one.

COMMON PART OF FOUR OTHER EMBODIMENTS

As was explained before, the agent of infection, such as virus, may rest in the syringe on the bumper 2, FIGS. 1 and 2 in between patients. For the infection to propagate to another patient, an infection agent from outside of drug cartridge must be sucked into the drug cartridge through the puncture in the diaphragm. To prevent that, in the prior art the syringe has to be sterilized for every new patient to kill any agent of infection present. The basic concept in the present invention is to dispose of the infection agent by making the bumper disposable and replaceable. In the prior art the bumper is an integral part of the syringe which is not disposable.

The implementation of this concept is to make the bumper an integral part of the needle assembly and to dispose of it together with the needle, which is the standard practice at present. This would save the cost of sterilizing the syringe. Since pre-sterilized needle assemblies and cartridges are being used, it will be impossible to accidentally have a non-sterilized bumper as can happen by mistaking a non-sterilized syringe for a sterilized one. Moreover, this will lessen the mental stress for personnel in dental office to constantly be aware of the possibility of a mistake.

These other embodiments of the invention add this and other features to the first embodiment. The difference between them is mainly in needle holders and needle assemblies. The other component of the drug injection system, the drug cartridge, is the same and is commercially available for all embodiments. Only the needle assemblies, needle holders or needle holder adapters and modifications of the barrel to accommodate them will be described. The rest of the system is the same as in the first embodiment.

Figure 23:
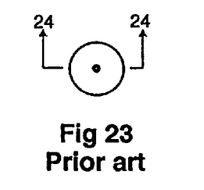
FIG. 23 Is an end view of a typical needle assembly of the prior art.
Figure 25:
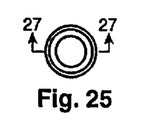
FIG. 25 Is an end view of the needle package shown in FIG. 26.

The typical needle assembly of the prior art is shown in FIGS. 23 and 24. Its body 33 has a hole with an internal thread and it is permanently attached to the needle 13. It is supplied in a pre-sterilized package shown in FIGS. 25, 26 and 27. The package is a capsule assembled from outlet cover 35 and intake cover 36. The needle assemblies of the present invention are adapted for packaging in the same or similar capsules.

Figure 7:
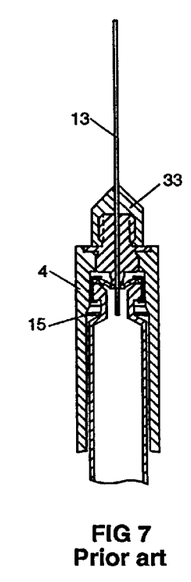
FIG. 7 Is a longitudinal section of the part of the syringe of FIG. 1, showing the deflection of the diaphragm of the cartridge as it occurs during injection.

A feature common to all four embodiments is the location of the disposable bumper in the syringe. When the disposable needle assembly is installed in the barrel, the bumper part of it is in the same place in relation to other parts of syringe, as is the permanent bumper 2 in the first embodiment. It works to the same effect as shown in FIGS. 6 and 7. A common feature of all embodiments is that all needle assemblies have an axis of symmetry which is their centerline and the needle is on this centerline. The contact surfaces on the molded barrel (or a needle holder adapter) with the disposable needle assembly may be wearing too fast in use. These parts may have metal inserts in such places.

Another common feature of the four embodiments is the shape of the end of bumper post 2 shown in FIG. 58 to FIG. 61.

The purpose of this invention is to prevent cross infection between patients by injection of drug, if the syringe has not been sterilized between patients. For this purpose it is crucial to minimize the leakage of the possibly contaminated drug during the aspiration procedure. Aspiration is accomplished by first pressing the bumper post 2 against the diaphragm to deflect it. This injects a small volume of drug into the patient's tissue. When the pressure on the bumper is relieved, the diaphragm reverts to the original position, sucking back (aspiring) automatically into the transparent drug cartridge the same volume of patient's body fluids as the volume of injected drug in the preceding step of injection procedure. This enables the dentist to see whether there is any blood in it. Body fluid sucked back into the cartridge may be contaminated.

Figure 60:
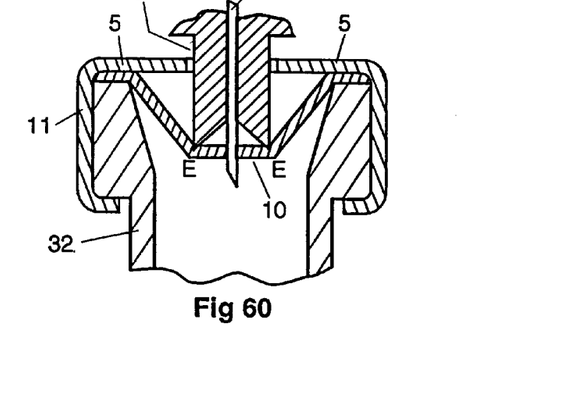
FIG. 60 Is a longitudinal cross section of the end of drug cartridge of FIG. 61. It shows the diaphragm 10 of drug cartridge 32 deflected by the bumper post 2.
Figure 61:
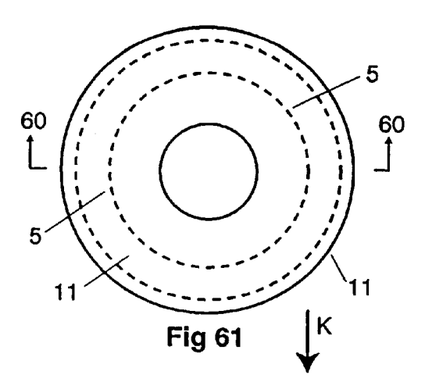
FIG. 61 Is the view at FIG. 60 in direction K. The bumper post is not shown.

During this aspiration procedure the drug may leak out through the puncture made by needle 13 in the diaphragm 10 of the drug cartridge 32, FIG. 60. The leakage may be caused by stretching the puncture together with the diaphragm when it is deflected by the bumper 2. What leaks out may be the carrier of infection. The novel idea incorporated in this invention is to minimize this leakage to the extent that what little leaks out, stays on the bumper and the diaphragm of drug cartridge. What leaks out is thrown out with the needle and drug cartridge before it can be deposited on the barrel of the re-usable self-aspirating syringe.

Figure 59:
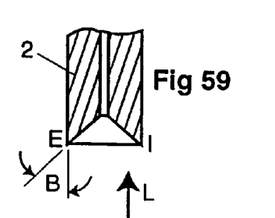
FIG. 59 Is a longitudinal cross section of FIG. 58.

The extent of the stretching of the puncture is very much dependent on the shape of the end of bumper 2 in contact with the diaphragm. Another idea incorporated in the present invention is to prevent stretching of the puncture even when the diaphragm as a whole is being stretched. This is accomplished with the shape of the end of bumper 2 as shown in FIG. 59. The square end of bumper has a conical recess 65 which forms a circular ridge with an acute angle B at the crest (edge) E—E of this ridge. This crest is in a plane at right angle with respect to the longitudinal direction of the bumper 2.

When the bumper 2 is pressed against the diaphragm 10, FIG. 60, it makes a line contact with the diaphragm 10 along the flat circle E—E. The diaphragm (and the puncture in it) within this circle E—E is stretched minimally, because the crest E—E of the ridge bites into the diaphragm and prevents its sliding over the ridge in a radial direction away from the needle 13. Only the diaphragm outside of the circle E—E is being stretched.

Tests have shown that with the shape of the end of bumper as in FIG. 59 and the ridge angle B being between 45 and 60 degrees, the leakage was observed on the average in about 2% of trials and it was so little that it was barely visible. What leaked out stayed on the surface of bumper 2 and of diaphragm 10 and after single use was thrown away with the bumper and drug cartridge. No contaminated drug was deposited on the barrel of the reusable self-aspirating syringe thereby eliminating the possibility of cross infection, even if the syringe has not been sterilized between patients.

With the other shapes of the end of bumper, such as rounded or pointed, the leakage was unacceptable for safety. Even with the shape of bumper as in FIG. 59, the leakage became unacceptable, if the same bumper was used repeatedly and the crest of ridge became disfigured by wear or corrosion.

In the self-aspirating syringes of the prior art, which have the same kind of needle holder as in the first embodiment, FIG. 2, the bumper 2 is a permanent and integral part of the needle holder and of syringe as a whole. It is exposed to corrosive action of the leaked drug. Even if it is made of stainless steel, it eventually corrodes and the whole needle holder has to be replaced from time to time. As it corrodes, its shape gradually changes to an irregular one and this increases the drug leakage from the puncture in the diaphragm. The performance of the syringe is already degraded long before the needle holder is replaced. The same thing is expected to happen with bumpers in the first embodiment of this invention, if they are made from stainless steel.

In the other four embodiments of this invention to be described, the bumper is new for every patient and the performance of the syringe will not degrade with time. This is in addition to the advantage that the infection carrier, which is the bumper, is disposable and, henceforth, the syringe is safe to use if not sterilized. Moreover, since the needle assembly with integral bumper and the drug cartridge are pre-sterilized at the factory by automated equipment, there is no possibility of them not being sterilized by human error.

MORE ABOUT ALIGNMENT AND LEAKAGE

To prevent infection by injection of drug, the drug leakage through the puncture in the diaphragm of drug cartridge must be eliminated. The leakage may be caused, as it was explained before, by puncturing the diaphragm off center.

Figure 62:
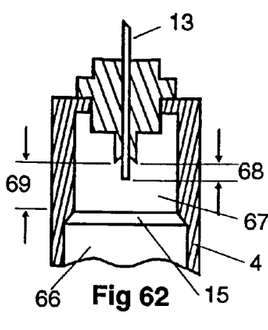
FIG. 62 Is the cross-section of the needle end of self-aspirating syringe, showing the cavity 67 close fitting the cap of drug cartridge.

The drug cartridge fits loosely inside the main portion 66 of the syringe barrel 4, FIG. 62. This is necessary because in the manufacture of cartridges, the outside diameter of them cannot be kept within close tolerance, besides, the cartridge may not be perfectly straight. The outside diameter of the metal cap 11 of the cartridge 32 can be kept within close tolerance.

The needle of this invention is designed for use with self-aspirating syringe. In such syringe the inside portion 67, FIG. 62, of the barrel 11 close to the bumper 2 is of reduced diameter for close fit with the cap 11 of cartridge. The inside spaces 66 and 67, FIG. 62, of the inside of the barrel are of different diameters and are separated by step 15, FIG. 62. This step is also visible in FIG. 2.

For the needle to puncture the diaphragm in the center, it is necessary that the cap is already inside of space 67, and is guided closely before the needle punctures the diaphragm. To obtain this, the distance 68 (from the end of bumper to the tip of needle) must be smaller than the distance 69 from the end of bumper to the step 15, FIG. 62.

This requirement is met when the length of needle protruding from the bumper is not longer than triple of the thickness of diaphragm 10, FIG. 62. If the protruding length of the needle is longer than that, the diaphragm may be punctured before the cap enters space 67 and is centered by it. In such a case the puncture in the diaphragm may be off center with the resulting leakage of drug.

The requirement that the end of the needle protruding from the bumper is not longer than the triple thickness of diaphragm is essential for attaining the purpose of this invention which is prevention of cross-infection. Commercially available dental needles are not made specifically for self-aspirating syringes and they do not meet this requirement.

The needle of the present invention is safe to use, because either normally there is no leakage through the puncture, or it is so insignificant that whatever leaks out stays on the bumper and is thrown away together with the needle and drug cartridge, so that there is no contaminated drug deposited on the syringe.

THE SECOND EMBODIMENT

Figure 35:
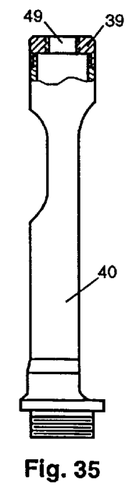
FIG. 35 Is a side elevation view, partly in cross section, of the assembly of the barrel of FIG. 33 with needle holder as in FIG. 31.
Figure 36:
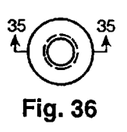
FIG. 36 Is an end view of the barrel assembly of FIG. 35..

The syringe part of this drug injection system looks like the syringe in FIGS. 1 and 2, with the exception that the needle holder is different and that the barrel end is modified to suit a different holder. Instead of needle holder 1, like in FIG. 2, it has needle holder adapter 39, shown in FIGS. 32 and 35. The barrel 40, FIG. 33, has a male thread on its end. The needle holder adapter 39 is permanently fastened to it. The barrel assembly, like that shown in FIG. 35, instead of being assembled from two parts, 39 and 40, alternately can also be made as one piece.

Figure 28:
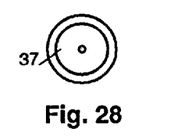
FIG. 28 Is an end view of needle assembly of FIG. 29.
Figure 29:
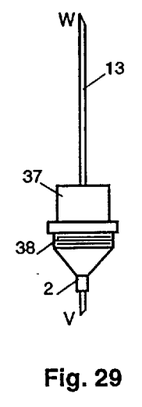
FIG. 29 Is a side elevation view of a first embodiment of the needle assembly of the present invention.
Figure 30:
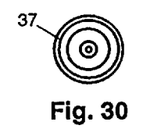
FIG. 30 Is an end view at the bumper end of the needle assembly of FIG. 29.
Figure 31:
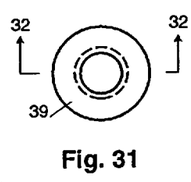
FIG. 31 Is an end view of the needle holder adapter used with needle assemblies of FIGS. 29 and 38.

The needle assembly is shown in FIGS. 28, 29 and 30. Its body, FIG. 29, has a male thread 38 which screws into female thread 48 in the needle holder adapter 39, FIG. 32. The body 37, FIG. 29, has a bumper 2, which is of the same shape and size as in the first embodiment.

Figure 27:
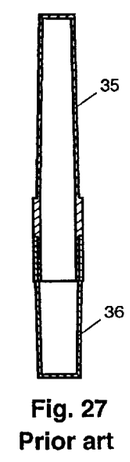
FIG. 27 Is a longitudinal section of the needle package of FIG. 26

The needle assembly of this embodiment is packaged the same way as in the prior art, that is it is fully covered by capsule's outlet and intake covers 35 and 36, FIG. 27. The installation of the needle assembly in the syringe is, as in prior art, done in three steps:

1. The capsule's intake cover 36, FIG. 27, is removed first from the intake end V of the needle assembly, FIG. 29. This exposes thread 38 on it.

2. The needle assembly is then screwed into the barrel assembly, FIG. 35, on the syringe.

3. The capsule's outlet cover 35 is removed from the output end W of the needle. This makes the syringe ready for injection.

THE THIRD EMBODIMENT

Figure 37:
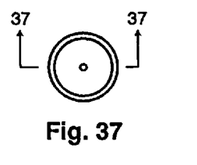
FIG. 37 Is an end view of a second embodiment of the needle assembly.
Figure 38:
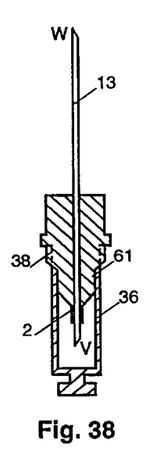
FIG. 38 Is a cross section of the needle assembly of FIG. 37.
Figure 39:
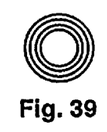
FIG. 39 Is the view on the capsule end of the needle assembly of FIG. 37.

The syringe in this embodiment is the same as in the second embodiment. The needle assembly for this embodiment is shown in FIGS. 37, 38 and 39. This needle assembly is similar to the second embodiment, FIG. 29, in that they both have an external thread 38 as means of attachment to the needle holder. The needle holder adapters in these two embodiments are similar too, in that they both have an internal thread. They look alike, so that they both are represented by the same FIG. 32.

The difference between the two needle assemblies is that the one of the second embodiment has a shank 61, FIG. 38. Packaging of the needle assembly in the third embodiment is different from that in the second. The shank 61 is there to mount the capsule's intake cover 36 on it. The package's outlet and intake covers 35 and 36, FIG. 27, cover the output end W and the intake end V of the needle, FIG. 38, separately. They may not overlap, leaving the thread 38 on the needle body exposed.

Figure 40:
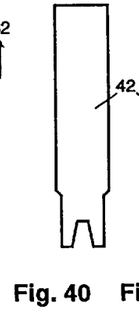
FIG. 40 Is a side elevation of the tool for removing capsule shown in FIG. 38.

The needle assembly is screwed into the needle holder with both covers still on. The intake cover 36 for the needle's intake end V is small enough to pass through the hole 49 of the needle holder, FIG. 35. It ends up inside of the barrel after installation. It can be removed with a tool 42 shown on FIGS. 40 and 41. If this cover is made long enough to protrude into side openings of the barrel, it can also be pulled off by gripping it between the thumb and index fingers.

In this drug injection system, the sterile bumper 2 and the intake end V of the needle, FIG. 38, cannot touch anything or be touched until they are mounted inside the barrel.

THE FOURTH AND THE PREFERRED EMBODIMENT

Figure 43:
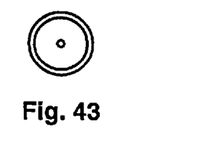
FIG. 43 Is an end view of the needle assembly of FIG. 42.
Figure 44:
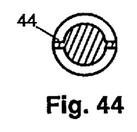
FIG. 44 Is a cross-section of FIG. 42 through the lugs.

In this preferred embodiment the syringe is the same as in the second embodiment, except that the needle assembly and the needle holder are different. They are shown on FIGS. 42, 43, 44, 45 and 46. The needle body has two lugs 44, FIGS. 43 and 44. They pass through the corresponding slots 45 in the needle holder, FIG. 46. When the needle assembly is inserted into a hole 47, in the needle holder 43, FIG. 45, and then turned clockwise, the lugs are catching on helical semi-circular tracks 46 on the backface of the hole. Turning the needle body further clockwise jams the lugs and locks the needle in place. Turning the body anti-clockwise releases it.

The advantage of this system is that the needle assembly can be locked in place in less than half a turn.

THE FIFTH EMBODIMENT

Figure 47:
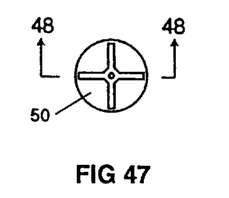
FIG. 47 Is an end view of the needle assembly of FIG. 48.
Figure 48:
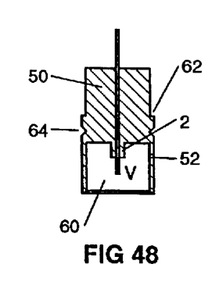
FIG. 48 Is a cross section of a fourth embodiment of the needle assembly of the present invention.
Figure 49:
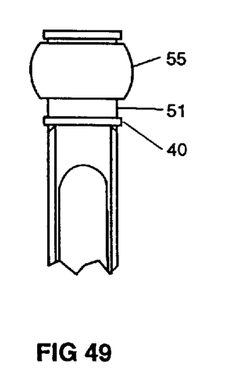
FIG. 49 Is a view of the end of a third embodiment of the syringe with the chuck open.
Figure 50:
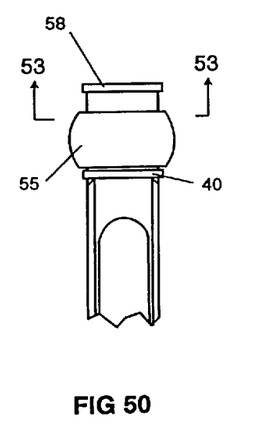
FIG. 50 Is a view of the end of syringe of FIG. 49 with the chuck closed.
Figure 51:
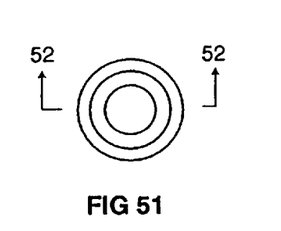
FIG. 51 Is the end view of FIG. 50.

In this embodiment the syringe is the same as in the second embodiment, except that the needle assembly 50 is like the one shown on FIGS. 47 and 48 and except that the needle holder is different. The needle assembly does not have thread as means of attachment. The needle holder is a special kind of chuck combined with an extension of the syringe barrel, as shown on FIGS. 49, 50, 51 and 52. Integral extension 51 of the syringe barrel serves as part of the chuck.

Figure 26:
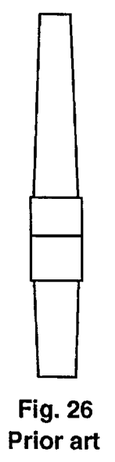
FIG. 26 Is a common commercial needle package.

The needle assembly 50 comes in a two-part pre-sterilized capsule, like one shown on FIGS. 26 and 27. Drug cartridges come also in pre-sterilized packages.

The needle assembly has a skirt 52 which surrounds both the bumper 2 and the intake end V of the needle, FIG. 48. The primary purpose of the skirt is to provide sterile surroundings for the bumper 2 and for the puncture in the diaphragm of the drug cartridge. The skirt end of the needle assembly 50 is inserted into the open end 53 of the barrel, FIG. 52, and pushed up against a step 54 in the opening 53 of the barrel. The skirt 52 fits closely inside of barrel opening 53, whereas the size of the inside opening 60 in the skirt is such as to provide a close fit for the cap 11, FIG. 5, of the drug cartridge.

Thus the skirt, apart from its primary purpose, serves additionally the purpose of reducing the inside diameter at the end of barrel, the same as step down 15, FIG. 2, in all other embodiments of the invention where there was no skirt. This has the same effect of centering the cap 11 with respect to the needle, as it was described in the preceding for the first embodiment. See FIG. 7.

Figure 5:
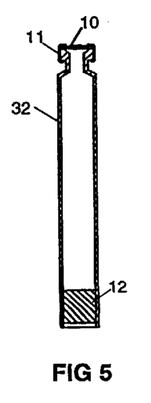
FIG. 5 Is a longitudinal section of the drug cartridge of FIG. 4.

Prior to injection, the cap 11 of the drug cartridge, FIG. 5, enters the opening 60 on the end of skirt, FIG. 48, and closes it off. The resulting configuration is similar to one shown on FIG. 7 which is for the first embodiment. Before the needle end V punctures the diaphragm and during the injection procedure, both the bumper 2 and the needle end V are fully enclosed in what is virtually a chamber, all walls of which, that is the inside of skirt 52 and the end face of cap 11, are pre-sterilized and disposable.

Any infection agent originating with the current patient, in case such agent may escape from the cartridge and be deposited on the bumper 2, will be disposed together with the used drug cartridge and needle assembly. A new virtual chamber (with a new bumper) is used with subsequent patient. The syringe as a whole does not have to be sterilized, because this would not improve the sterile environment where it matters, that is inside the pre-sterilized chamber.

Figure 55:
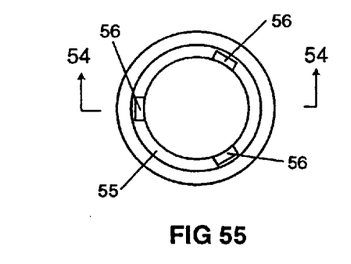
FIG. 55 Is an end view of FIG. 54.

The chuck is to secure the needle assembly 50, inserted into the end of barrel, such that it does not fall out. It comprises lock ring 55, FIG. 52, three jaws 57 and a flange 58. The latter is fastened into the end of barrel 51. The lock ring has cam surfaces 56 in three recesses, FIG. 55. The jaws, FIGS. 56 and 57, have corresponding cam surfaces on their outer sides. When the lock ring 55 is in the position shown on FIG. 49, the jaws 57 are free floating. The end of skirt 52, when inserted into the barrel, pushes them out of the way. When the lock ring 55 is pushed into position shown on FIG. 50, first the cam surfaces R, FIG. 56, and then the cam surfaces L become engaged, pushing the jaws towards the center of the barrel first and then locking the needle assembly in the barrel.

Figure 56:
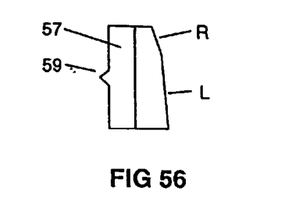
FIG. 56 Is a side view of the chuck jaw.
Figure 57:
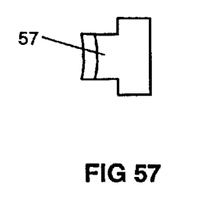
FIG. 57 Is an end view of FIG. 56.
Figure 58:
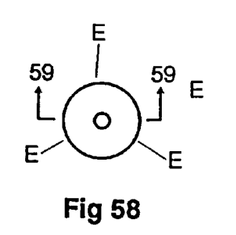
FIG. 58 Is the end of bumper post. It is a view in direction L at FIG. 59.

The ridges 59 on the jaws, FIG. 56, enter the groove 64 on the needle assembly, FIG. 48. This is merely to secure that the needle assembly does not fall out, if the lock ring 55 is not tightened properly. Even without the ridges 59 and the groove 64, the jaws 57 clamp the needle assembly 50 sufficiently tight to keep it in place.

The OD (outside diameter) of the skirt is the largest cross dimension of the needle assembly (that is one measured at right angle to the needle). The outlet cover 35, FIG. 27, of the package rests against the step 62 on the body, FIG. 48. The OD of this outlet cover is slightly larger than the OD of the skirt. The intake cover 36 is overlapping on it. Since the outlet cover is not removed until after installation of the needle assembly, the clearance for it is provided on the ID of barrel, visible as a step 63, FIG. 52.

COMPARISON OF DIFFERENT EMBODIMENTS

Although the fifth embodiment is designated as the preferred one, this choice is purely arbitrary. Which embodiment is practically the best will be determined by the manufacturing costs, expert opinion of users, opinion of medical authorities and, perhaps, by the results of tests in a research lab for the infection agents.

DEFINITION OF TERMS USED IN CLAIMS

Figure 32:
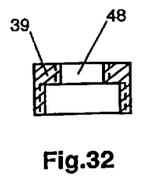
FIG. 32 Is a cross section of needle holder adapter of FIG. 31.
Figure 33:
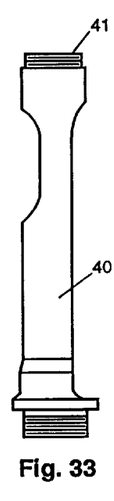
FIG. 33 Is a side elevation view of the second embodiment of the barrel of syringe of the present invention.
Figure 34:
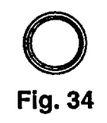
FIG. 34 Is an end view of the barrel of FIG. 33.
Figures 41, 45, 46:
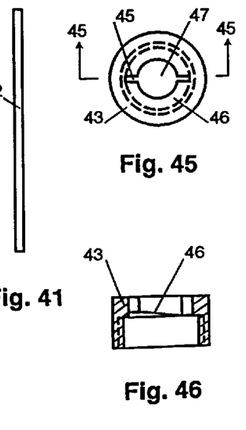
FIG. 41 Is a further side view of the tool of FIG. 40.
FIG. 45 Is an end view of needle holder adapter of FIG. 46.
FIG. 46 Is a cross section of the needle holder adapter used with needle assembly of FIG. 42.
Figure 42:
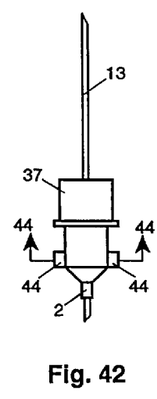
FIG. 42 Is a side elevation view of a third embodiment of the needle assembly.
Figure 52:
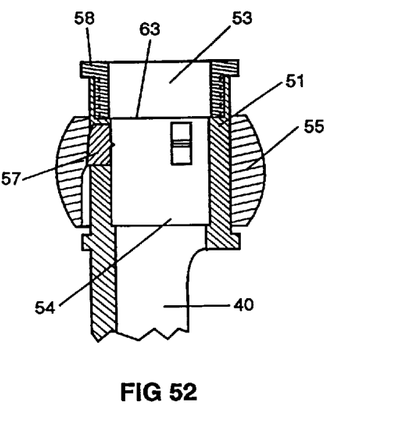
FIG. 52 Is a longitudinal section of FIG. 51.
Figure 53:
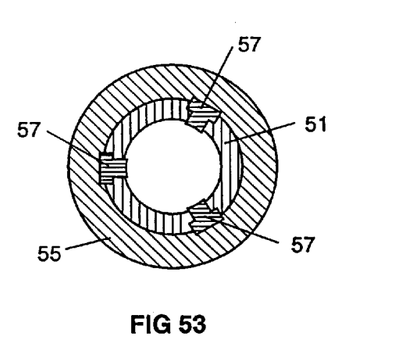
FIG. 53 Is a cross section of FIG. 50.
Figure 54:
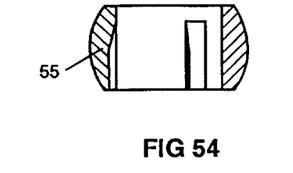
FIG. 54 Is a longitudinal section of the lock ring of FIG. 55.

Means for attachment of a needle assembly include: 1) needle holder combined with the bumper, like 1, FIG. 2, 2) female thread in the first (delivery) end of barrel, 3) female thread in needle holder adapter, like 39, FIG. 32, 4) needle holder adapter with cam lock, like 43, FIG. 46, 5) jaw chuck assembly like the one shown on FIG. 52. They all have an axis of symmetry which is also their centerline.
Barrel
   May include permanent assembly of a single piece barrel with means for attachment of needle assembly.
Centerline of a fingergrip
   Is the centerline of mounting means or round hole in fingergrip coincident with centerline of barrel upon assembly.
Needle assembly
   Comprises a needle (hypodermic tubing) and a body permanently joined with it. Needle assembly has an axis of symmetry, which is also a centerline of the needle assembly. The needle is on this centerline.
Needle body may include:
   1) Mounting means (releasable) like female thread 33, FIG. 24, or male thread like 38, FIGS. 29 and 38, or lugs like 44, FIG. 43, or outer surface of the skirt 52 for clamping on, or recess 64, FIG. 48;
   2) A shank like 61 in FIG. 38;
   3) A seating surface, for example, like a flange shown in FIGS. 29, 38 and 43;
   4) A projection (bumper) like 2 in FIGS. 2, 29, 38, 43 and 48. This projection is on all embodiments of the needle body.
Means of attachment of a finger grip
   Include male thread on the second end of barrel, like shown on FIG. 11. Its axis of symmetry is also its centerline.
Seating surface
   Includes a flange, a shoulder or a change in diameter to provide a contact area with another surface upon assembly.
Plunger rod actuation means
   Includes thumb ring.

What is claimed is:

1. A needle assembly for use with a reusable syringe for single use drug cartridges containing a liquid drug, the drug cartridge being closed at one end with a piercable diaphragm secured to the cartridge by a metal cap having a central opening therein, the needle assembly comprising,
   a needle body having a mounting means for releasably mounting the needle assembly in the barrel of a reusable syringe,
   a double-ended needle passing through and permanently attached to the body and having a first intake end for insertion into a single use drug cartridge by piercing the diaphragm and a second outlet end for delivery of the drug to the patient, the needle body being provided with a bumper post through which the first intake end of the needle passes, the bumper post being of a size to pass through the opening in the cap of a drug cartridge and having a generally cylindrical shape with a concave contact end face to provide a contact edge at the periphery of the bumper post capable of directly contacting an area of a surface of the diaphragm of a drug cartridge along the contact edge spaced away from the point of insertion of the first intake end of the needle through the diaphragm, the contact end face of the bumper post being capable of sufficiently deflecting the area of the surface of the diaphragm towards the interior of the cartridge to displace a volume of a liquid drug in a drug cartridge greater than an internal volume of the double-ended needle to the extent that any colored body fluid, such as blood, if present in the contents returned to the drug cartridge when the diaphragm returns to its resting position, is clearly visible.

2. A reusable syringe for use with a single use drug cartridge, the syringe comprising a barrel having a means for releasably mounting a needle assembly according to claim 1 at one end and a finger grip at a second end, a plunger rod passing through the finger grip into the interior of the barrel and having an actuation means at an end exterior of the barrel and finger grip;

the finger grip having generally flat end surfaces and a central region having a generally concave surface located between said end surfaces for gripping by a user's fingers, the central region being joined to the end surfaces by a gradual transition from a concave to a convex surface.

3. A reusable syringe as claimed in claim 2 wherein the barrel has an exterior flange on the second end which mates with a recess on the surface of the finger grip to provide an alignment stop for mounting of the finger grip to the barrel.

4. A needle assembly as claimed in claim 1 wherein the needle body is provided with a shank located between the mounting means and the bumper post the needle assembly further being provided with a capsule attached to the shank and covering and protecting the first intake end of the needle, the capsule being of a size to pass through the opening in a barrel and into the interior of a barrel whereby the capsule is removed from the needle assembly after the needle assembly is mounted on a syringe.

5. A needle assembly as claimed in claim 1 wherein the needle assembly is provided with a skirt surrounding the intake end of the needle, the skirt having an external diameter to enable it to pass through an end and into the interior of a barrel when the needle assembly is mounted on a barrel, the skirt having an internal diameter to closely fit a cap of a single use drug cartridge.

6. A needle assembly as claimed in claim 5 wherein the external diameter of the needle assembly at any place is not larger than the external diameter of the skirt.

7. A needle assembly as claimed in claim 5 wherein the needle body is provided with a shank located between the mounting means and the bumper post, the needle assembly further being provided with a capsule attached to the shank and covering and protecting the first intake end of the needle, the capsule being of a size to pass through the opening in a barrel and into the interior of a barrel whereby the capsule is removed from the needle assembly after the needle assembly is mounted on a syringe.

8. A needle assembly as claimed in claim 1 wherein the mounting means comprises an annular recess on the needle body for receiving jaws of a chuck in the barrel of a syringe for releasably locking the needle assembly to the syringe.

9. A needle assembly as in claim 1, wherein the tip of the first intake and of the double ended needle passing through the bumper post sticks out from the end of bumper post not more than the triple thickness of the diaphragm of the drug cartridge.

10. A needle assembly as claimed in claim 1 wherein the contact end face of the bumper post is a sharp contact edge at the periphery of the bumper post capable of contacting the diaphragm along a closed circular line spaced away from the point of insertion of the first intake end of the needle through the diaphragm.

11. A needle assembly as claimed in claim 1 wherein the mounting means comprises lugs which mate with a cam surface on a barrel of a syringe.

* * * * *